(12) United States Patent
Kalafsky

(10) Patent No.: US 7,763,655 B2
(45) Date of Patent: Jul. 27, 2010

(54) COSMETIC COMPOSITIONS HAVING CARNITINE CREATINATE AND METHODS FOR USING

(75) Inventor: Robert E. Kalafsky, Ogdensburg, NJ (US)

(73) Assignee: Avon Products, Inc, New York, NY (US)

( * ) Notice: Subject to any disclaimer, the term of this patent is extended or adjusted under 35 U.S.C. 154(b) by 35 days.

(21) Appl. No.: 11/880,167

(22) Filed: Jul. 20, 2007

(65) Prior Publication Data

US 2007/0264205 A1 Nov. 15, 2007

(51) Int. Cl.
- A01N 37/12 (2006.01)
- A01N 37/52 (2006.01)
- A61K 31/155 (2006.01)
- A61K 31/13 (2006.01)
- A61K 8/02 (2006.01)

(52) U.S. Cl. .................. 514/566; 514/631; 514/663; 424/401

(58) Field of Classification Search .............. 514/566, 514/631, 663; 424/401
See application file for complete search history.

(56) References Cited

U.S. PATENT DOCUMENTS

| | | | |
|---|---|---|---|
| 5,994,581 A | 11/1999 | Fang | |
| 6,432,424 B1 | 8/2002 | Shapiro et al. | 424/59 |
| 6,653,504 B1 | 11/2003 | Buononato | |
| 2002/0044913 A1 | 4/2002 | Hamilton | 424/59 |
| 2002/0106388 A1 | 8/2002 | Pugliese | 424/401 |
| 2003/0215506 A1 | 11/2003 | Kuhrts | |
| 2004/0029969 A1 | 2/2004 | Blatt et al. | 514/565 |

FOREIGN PATENT DOCUMENTS

| | | |
|---|---|---|
| FR | 2694195 A1 | 2/1994 |
| JP | 2001064147 A | 3/2001 |
| WO | 0117948 A1 | 3/2001 |
| WO | 0211717 A1 | 2/2002 |
| WO | 2004/074216 A2 | 9/2004 |

OTHER PUBLICATIONS

Rosenbaum et. al., Plastic and Reconstructive Surgery, 1998, Journal of the American Society of Plastic Surgeons, vol. 101, pp. 1934-1939.*
Ronald M. DiSalvo; Cellulitis Control, Efficacy of Xanthines, Silanes, CoA, L-Carnitine and Herbal Extracts in Reducing Cellulitis, 1996, Cosmetics and Toiletries, Edizione Italiana, vol. 17, No. 4, pp. 33, 35-37 and 39-41 (abstract only).
Tholon et al.; An In Vitro, Ex Vivo, and In Vivo Demonstration of the Lipolytic Effect of Slimming Liposomes: An Unexepcted a2-Adrenergic Antagonism, 2002, Journal of Cosmetic Science, vol. 53, No. 4, pp. 209-218 (abstract only).
Dragomirescu et al.; A New Anticellulitic Formula Based on Carnitine, 2003, Espanol de la Detergencia, vol. 33, pp. 317-323 (abstract only).
Bushkin et al., "*The Raw Facts: The Latest in Raw Material Trends and Developments*", Cygnus Publishing; Abstract only, Aug. 2002.

\* cited by examiner

*Primary Examiner*—Sreeni Padmanabhan
*Assistant Examiner*—Sarah Pihonak
(74) *Attorney, Agent, or Firm*—Charles J. Zedler; Joan M. McGillycuddy; Anthony M. Santini

(57) ABSTRACT

There is a topical composition having carnitine creatinate and a cosmetically acceptable vehicle. There is also provided a method for improving the aesthetic appearance of skin. There is also provided a method for inhibiting the induced lipid synthesis in skin. There is also provided a method for inhibiting the formation of cellulite in skin.

10 Claims, No Drawings

COSMETIC COMPOSITIONS HAVING CARNITINE CREATINATE AND METHODS FOR USING

BACKGROUND OF THE INVENTION

1. Field of the Invention

The present invention relates to a topical composition that improves the aesthetic appearance of skin. The present invention also relates to a topical composition that inhibits induced lipid synthesis in skin. The present invention further relates to a topical composition that inhibits the formation of cellulite in skin.

2. Description of the Related Art

Fat may build up underneath the surface of the skin due to induced lipid synthesis in the adipose layer of the skin. The buildup may take the form of a multiplicity of small but recognizable pockets of fat underneath the surface of the skin. Such buildup is commonly referred to as cellulite. Cellulite may impart an unnatural appearance to the skin. Skin can appear lumpy and discontinuous.

It would be desirable to have a topical composition that inhibited induced lipid synthesis in the skin. It would also be desirable to have a topical composition that inhibited the formation of cellulite in skin. It would further be desirable to have a topical composition that improves the aesthetic appearance of skin.

SUMMARY OF THE INVENTION

It is an object of the present invention to provide a topical composition that improves the aesthetic appearance of skin.

It is another object of the present invention to provide a topical composition that inhibits the induced lipid synthesis in skin.

It is still another object of the present invention to provide a topical composition that inhibits the formation of cellulite in skin.

It is yet another object of the present invention to provide a topical composition having carnitine creatinate and a cosmetically acceptable vehicle.

It is a further object of the present invention to provide a method for improving the aesthetic appearance of skin by providing a composition having a cosmetically acceptable vehicle and an effective amount of carnitine creatinate that is topically applied to the skin.

It is yet a further object of the present invention to provide a method for inhibiting induced lipid synthesis in skin by providing a composition having a cosmetically acceptable vehicle and an effective amount of carnitine creatinate that is topically applied to the skin.

It is still yet a further object of the present invention to provide also a method for inhibiting the formation of cellulite in skin by providing a composition having a cosmetically acceptable vehicle and an effective amount of carnitine creatinate that is topically applied to the skin.

DETAILED DESCRIPTION OF THE INVENTION

The active ingredient in the composition is carnitine creatinate. Carnitine creatinate is represented by the following structure:

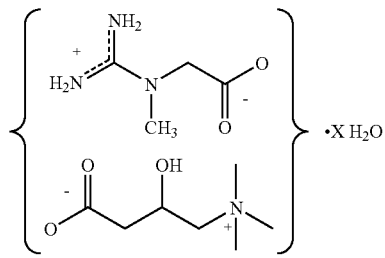

wherein X is an integer of 0 to about 5.

Carnitine creatinate is a salt of the acid-base reaction between carnitine and creatine. Carnitine creatinate is available commercially as a 100% active from American International Chemical, Inc. Carnitine creatinate is further described in U.S. Pat. No. 5,994,581, which is incorporated herein by reference in its entirety.

The carnitine creatinate is present in an amount effective to improve the aesthetic appearance of skin. The carnitine creatinate may also be present in an amount effective to inhibit induced lipid synthesis. The carnitine creatinate may further be present in an amount effective to inhibit formation of cellulite. Preferably, the carnitine creatinate is present at about 0.01 wt % to about 25 wt % based on the total weight of the composition. More preferably, the carnitine creatinate is present at about 0.05 wt % to about 10 wt %. Most preferably, the carnitine creatinate is present at about 0.1 wt % to about 5 wt %.

Compositions useful in the present method have a vehicle that is pharmaceutically or cosmetically acceptable. Such vehicles include, but are not limited to, one or more lower alcohols, fatty alcohols, fatty ethers, fatty esters, isododecane, polyols, glycols, liposomes, laminar lipid materials, water, or any combinations thereof.

The composition may take any product form known in the art. Useful forms include, but are not limited to, aerosol spray, cream, lotion, gel, foam, ointment, mask, mousse, patch, powder, pump spray, stick, tape, towelette, and pomade. Liquid forms of the composition may be any type, such as a solution, suspension, dispersion, or emulsion. Useful emulsion forms include oil-in-water, water-in-oil, silicone-in-water, water-in-silicone, and triple emulsions. The composition may be aqueous or anhydrous.

Compositions may also include one or more of the following optional ingredients: amino acids, anesthetics, anti-acne agents, anti-allergenics, antifungals, antimicrobials, anti-inflammatory agents, anti-irritants, antioxidants, antiseptics, antivirals, chelating agents, colorants, depigmenting agents, emollients, emulsifiers, exfoliants, for example, α-hydroxy acids such as lactic acid and glycolic acid, β-hydroxy acids, sugar acids, oxa acids, and oxa diacids, film formers, fragrances, humectants, hyper- and hypopigmenting agents, self-tanning agents, insect repellents, lubricants, moisturizers, peptides, pharmaceutical agents, photostabilizing agents, preservatives, retinoids, vitamins and vitamin derivatives such as niacin (nicotinic acid) and ascorbic acid and its derivatives, salicylic acid, skin protectants, skin penetration enhancers, staining agents, sunscreens, stabilizers, surfactants, thickeners, viscosity and/or rheology modifiers, or any combinations thereof.

The composition is also useful in preventing, ameliorating or treating acne; preventing, ameliorating or treating oily skin; preventing, ameliorating or treating oily hair; preventing, ameliorating or treating oily scalp; preventing, ameliorating or treating skin blemishes; preventing, ameliorating or treating skin breakouts; and improving skin texture.

The composition may be applied to the skin one or more times per day as needed or desired. If desired, the composition may be applied twice or more per day. Generally, the composition is applied as often as needed to impart and maintain a desirable aesthetic appearance to the skin or to maintain a skin appearance substantially free of cellulite. Typically, beneficial results are observed following daily application of the topical composition for a period of one week, preferably two weeks, especially four weeks, and most preferably after eight weeks.

In another aspect of the invention, there is a hydrogel patch that incorporates the carnitine creatinate, which is admixed with the hydrogel base. The patch can be affixed to an area of the skin of the user in need of fat reduction, for example, the inner thigh of the user. The patch is applied to the skin for a period of time effective for treatment, e.g., four or more hours per day for one day or two days, after which time the patch is removed. A second patch is then affixed, and the process is repeated over an extended period of time, i.e., about four weeks, preferably eight weeks, and most preferably 12 weeks.

In view of the foregoing, it is surprising that the aesthetic appearance of the skin can be improved by the topical application of the compositions of the present invention. It is further surprising that induced lipid synthesis in the skin can also be inhibited by the topical application of the compositions of the present invention. It is still further surprising that the formation of cellulite can be inhibited by such topical application.

The following are examples of the present invention. Unless otherwise indicated, all percentages or parts are by weight.

EXAMPLES

Examples 1 and 2

Compositions of the present invention in gel (Composition A) and cream (Composition B) forms are prepared. Ingredients of the compositions are set forth in Table 1 below.

TABLE 1

| Ingredients | Composition A (Gel) (Wt. %) | Composition B (Cream) (Wt. %) |
|---|---|---|
| Carnitine creatinate | 0.1-5.0 | 0.1-5.0 |
| Glycerin | 3.0-5.0 | 3.0-7.0 |
| Propylene glycol | 1.0-3.0 | |
| Thickener | 0.5-1.0 | 0.5-1.0 |
| Ethanol | 0.1-5.0 | |
| Emulsifier | | 1.0-10.0 |
| Oil | | 1.0-10.0 |
| Ester | | 1.0-10.0 |
| Wax | | 0.1-5.0 |
| Silicone oil | | 0.1-5.0 |
| Powder | | 0.0-2.0 |
| Preservative | 0.1-0.7 | 0.1-0.7 |
| Water | QS 100.0% | QS 100.0% |

Composition A is prepared by admixing the ingredients together at 25° C. to 30° C. and allowing the mixture to thicken to form a gel.

Composition B is made by forming an aqueous phase premix of water and water soluble components, which premix is heated to 80° C. and an oil phase premix of oil, silicone, wax, ester components, and an emulsifier, which premix is heated to 80° C. The oil phase is then blended with the water phase, and cooled to room temperature.

Compositions A and B are applied to areas of the body in need of fat reduction, in particular to the arms, thighs, and buttocks. Compositions A and B are applied daily for a period of time, typically about eight weeks, to effect an improvement in the appearance of the skin, in particular, an observable reduction in fat density, circumference and the unwanted appearance of cellulite.

Example 3

A hydrogel patch is prepared by premixing the carnitine creatinate and the hydrogel base. The patch is affixed to the area of the skin of the user in need of fat reduction, for example, the inner thigh of the user. The patch is removed after 1 to 2 days and a second patch is then affixed. The process is then repeated over a period of eight weeks.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for reducing the formation of cellulite in skin, comprising: topically applying to the skin a composition having a cosmetically acceptable vehicle and an effective amount of carnitine creatinate.

2. A method for reducing fat on the arms, thighs and/or buttocks comprising: topically applying to skin of the arms, thighs and/or buttocks a composition having a cosmetically acceptable vehicle and an effective amount of carnitine creatinate.

3. The method of claim 1, wherein the carnitine creatinate is present at about 0.05 wt % to about 10 wt % based on the total weight of the composition.

4. The method of claim 2, wherein the carnitine creatinate is present at about 0.05 wt % to about 10 wt % based on the total weight of the composition.

5. The method of claim 2, wherein the carnitine creatinate is present at about 0.1 wt % to about 5 wt % based on the total weight of the composition.

6. The method of claim 1, wherein the vehicle has an adjuvant selected from the group consisting of one or more lower alcohols, fatty alcohols, fatty ethers, fatty esters, isododecane, polyols, glycols, liposomes, laminar lipid materials, water, and any combinations thereof.

7. The method of claim 1, wherein the composition is in the form of a product selected from the group consisting of aerosol spray, cream, lotion, gel, foam, ointment, mask, mousse, patch, powder, pump spray, stick, tape, towelette, patch, and pomade.

8. The method of claim 1, further comprising one or more optional ingredients selected from the group consisting of amino acids, anti-acne agents, anti-irritants, antioxidants, chelating agents, colorants, hyperpigmenting agents, emollients, emulsifiers, exfoliants, film formers, fragrances, humectants, hypopigmenting agents, lubricants, moisturizers, peptides, vitamins, photostabilizing agents, preservatives, retinoids, skin protectants, skin penetration enhancers, sunscreens, stabilizers, surfactants, thickeners, viscosity and/or rheology modifiers, and any combinations thereof.

9. The method of claim 2, wherein the carnitine creatinate is present at about 0.01 wt % to about 25 wt % based on the total weight of the composition.

10. The method of claim 1, wherein the carnitine creatinate is present at about 0.01 wt % to about 25 wt % based on the total weight of the composition.

* * * * *